United States Patent
Wrublewski et al.

(10) Patent No.: US 6,174,309 B1
(45) Date of Patent: Jan. 16, 2001

(54) SEAL & CUT ELECTROSURGICAL INSTRUMENT

(75) Inventors: Thomas A. Wrublewski, Sharon; Kevin M. Allaire, Mattapoisett; William Frey, Kingston; Kevin Lemire, E. Douglas; Paul C. Nardella, Sr., Wareham, all of MA (US)

(73) Assignee: Medical Scientific, Inc., Taunton, MA (US)

(*) Notice: Under 35 U.S.C. 154(b), the term of this patent shall be extended for 0 days.

(21) Appl. No.: 09/248,484

(22) Filed: Feb. 11, 1999

(51) Int. Cl.$^7$ .................................................. A61B 18/18
(52) U.S. Cl. .................................. 606/45; 606/51; 606/52
(58) Field of Search .................................. 606/28–31, 41, 606/51, 52

(56) References Cited

U.S. PATENT DOCUMENTS

| | | |
|---|---|---|
| 2,002,594 | 5/1935 | Wappler et al. . |
| 2,004,559 | 6/1935 | Wappler et al. . |
| 4,209,017 | * 6/1980 | Shaw ........................ 606/28 |
| 4,492,231 | 1/1985 | Auth . |
| 4,655,216 | 4/1987 | Tischer . |
| 5,190,541 | * 3/1993 | Abele et al. ............... 606/46 |
| 5,443,463 | * 8/1995 | Stern et al. ................ 606/51 |
| 5,445,638 | * 8/1995 | Rydell et al. .............. 606/51 |
| 5,458,598 | 10/1995 | Feinberg et al. ............ 606/52 |
| 5,573,535 | * 11/1996 | Viklund ...................... 606/51 |
| 5,599,350 | 2/1997 | Schulze et al. .............. 606/51 |

(List continued on next page.)

OTHER PUBLICATIONS

United States Statutory Invention Registration Registration No.: H1745 Published: Aug. 4, 1998 Author: Paraschac Entitled: Electrosurgical Clamping Device with Insulation Limited Bipolar Electrode.

*Primary Examiner*—Michael Peffley
(74) *Attorney, Agent, or Firm*—Nutter, McClennen & Fish, LLP

(57) ABSTRACT

An electrosurgical instrument has a handle and a body which position and close a jaw about a tissue site for simultaneously cutting and sealing relatively large tissue structures. The jaw includes an electrosurgical cutting member, which may be a blade or wire, against which tissue is biased along a cut line, and a clamping assembly that clamps a region adjacent to or surrounding the cut line. The clamping assembly includes sealing electrodes for heating the region and welding tissue along the side of the cut as the cutter parts the tissue. The clamping assembly preferably has first and second clamping jaws extending in parallel to grip the tissue as tension is released by the cut, allowing dependable and complete sealing of the cut ends over an extended time while the tissue is immobilized. Sealing electrodes formed of thermally conductive material may be covered by a thinner coating or thermally non-impeding or heat transfer cover, which preferably includes a material to assure biocompatibility and prevent sticking. The handle, body and jaw may be configured in the shape of a hemostat to allow simple positioning, or may be configured with an elongated body and a mechanism that operates the jaw through a stationary or telescoping handle for endosurgical use through a small incision. The blade may extend entirely to the tip, or the clamp assembly may extend forward of the blade. An energy ratio input element may attach to an energy source to apportion electrosurgical energy between the cutting member and the sealing electrodes. The element may include a pair of transformers, or a transformer with a split secondary or a tapped secondary winding, with the primary configured for connection to the output of an RF scalpel drive console. The windings of the transformer match impedances and power requirements of the different cutting and sealing electrodes to coordinate effective tissue sealing and welding with the cutting operation.

18 Claims, 8 Drawing Sheets

U.S. PATENT DOCUMENTS

| | | | |
|---|---|---|---|
| 5,624,452 | 4/1997 | Yates | 606/139 |
| 5,665,085 | 9/1997 | Nardella | 606/41 |
| 5,674,220 | 10/1997 | Fox et al. | 606/51 |
| 5,688,270 | 11/1997 | Yates et al. | 606/51 |
| 5,693,051 | 12/1997 | Schulze et al. | 606/51 |
| 5,709,680 | 1/1998 | Yates et al. | 606/50 |
| 5,713,896 | 2/1998 | Nardella | 606/50 |
| 5,716,366 | 2/1998 | Yates | 606/139 |
| 5,735,848 | 4/1998 | Yates et al. | 606/48 |
| 5,735,849 | 4/1998 | Baden et al. | 606/51 |
| 5,755,717 | 5/1998 | Yates et al. | 606/51 |
| 5,797,941 | 8/1998 | Schulze et al. | 606/171 |
| 5,807,393 | 9/1998 | Williamson, IV et al. | 606/32 |
| 5,817,146 * | 10/1998 | Augustine et al. | 607/104 |
| 5,827,271 | 10/1998 | Buysse et al. | 606/40 |
| 5,871,479 * | 2/1999 | Furumoto et al. | 606/94 |
| 5,891,142 * | 4/1999 | Eggers et al. | 606/51 |

* cited by examiner

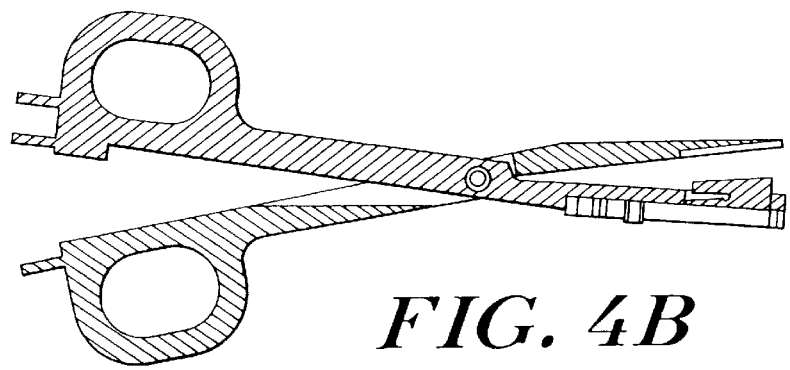
*FIG. 4B*
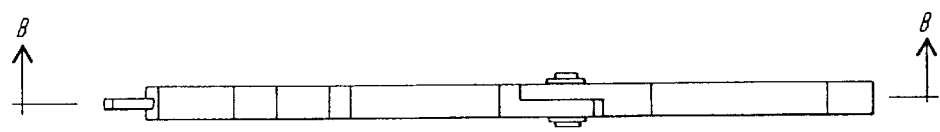
*FIG. 4A*
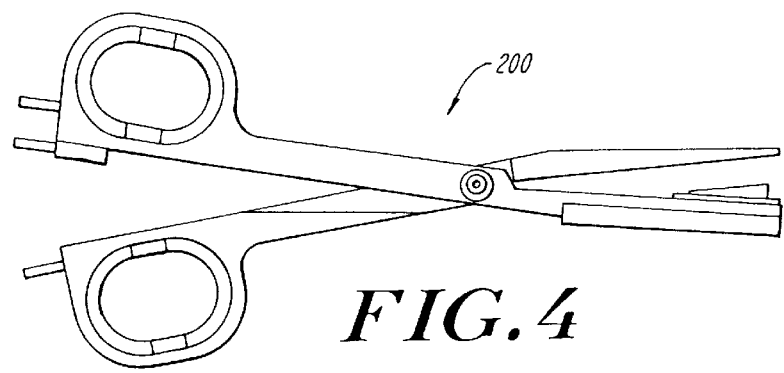
*FIG. 4*
 
*FIG. 4C*  *FIG. 4D*

FIG. 4E
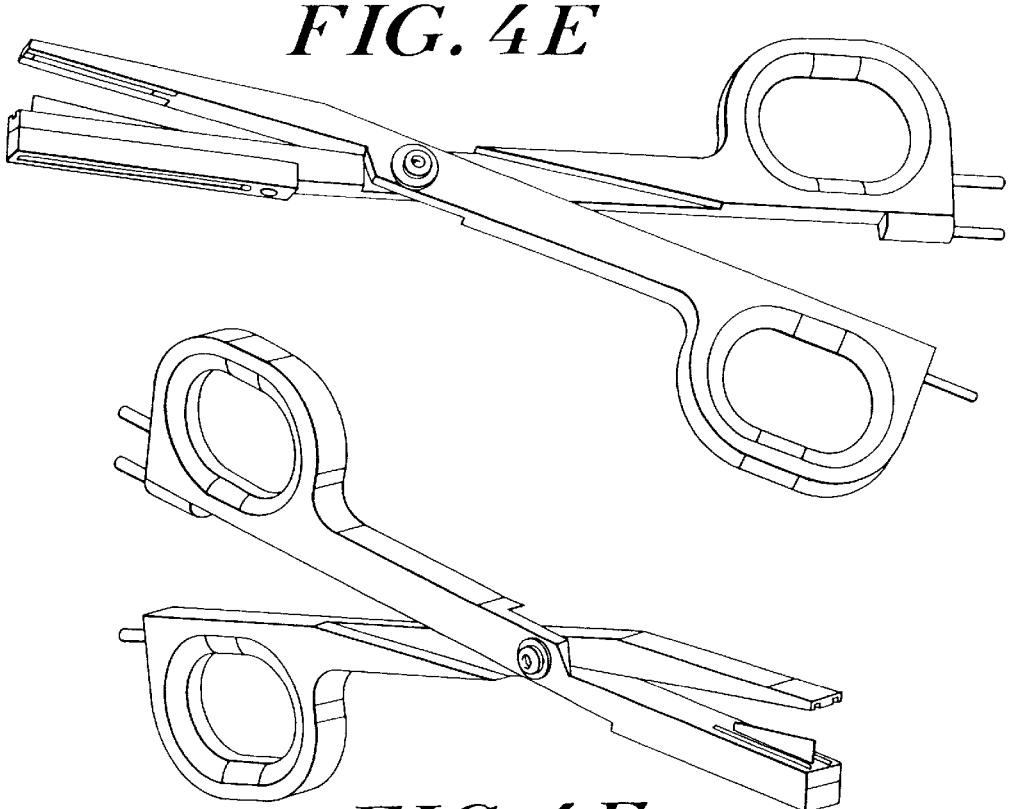
FIG. 4F
FIG. 4G
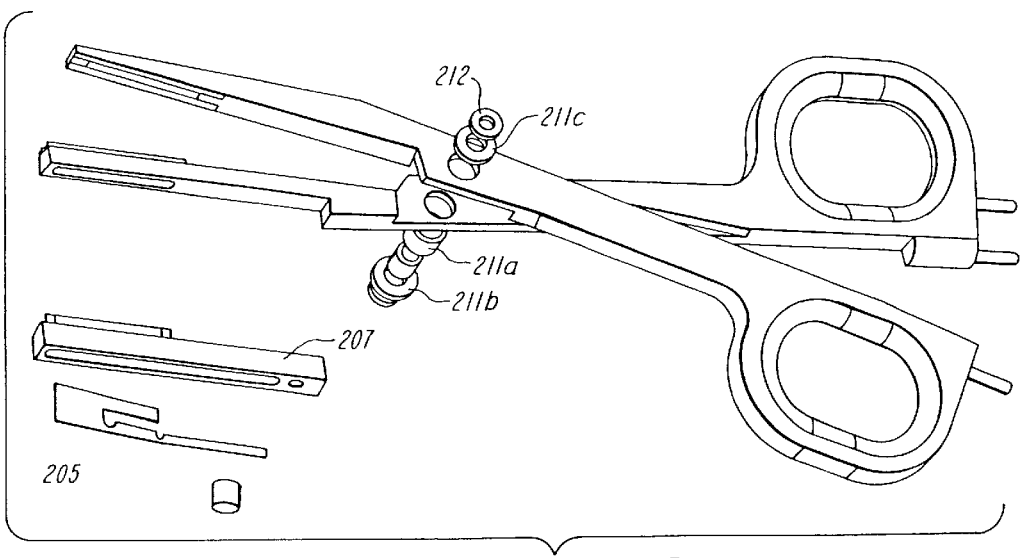

SEAL & CUT ELECTROSURGICAL INSTRUMENT

BACKGROUND OF THE INVENTION

The present invention relates to surgery and particularly to electrosurgical devices.

In general when performing any surgery the surgeon must be attentive to the presence of blood vessels in the tissue being cut. Depending on the circumstances, vessels may be tied off at two positions before being severed, or if severed unknowingly, may be stapled, clipped, tied off and/or coagulated after cutting. Several surgical instruments address commonly arising situations, for example by providing dual rows of staples surrounding a cutting blade to simultaneously sever and close a vessel or tubular organ. Furthermore, electrocoagulation has been used to seal vessels and prevent the flow of blood when cut. However coagulation relies upon generation of heat in the tissue by current flowing therein, and the degree of coagulation results from a complex balance of tissue impedance, heat transfer due to contact, perfusion etc., and the area and energy of the applied RF coagulation source, all of which will affect the degree of coagulation and the time required for effective treatment. In addition to RF coagulation, RF scalpels have also come into wide use. These operate by providing a high current over a sharp edge or small area so that the contact electrode acts as a blade and cuts tissue along the blade path. The contact electrode for an RF scalpel may in fact be blade shaped, and also perform physical cutting, although in practice such scalpels have an edge of finite width to present a defined level of electrical power.

One would expect that since an electrosurgical scalpel and a coagulation unit each rely on the provision of RF energy, combined instruments would be readily available. There have in fact been instruments designed for both purposes, for example a spatula-like scalpel which is useful both for small cauterization and for cutting operations. In general however, for larger surgery, suturing or clipping of vessels is still required prior to cutting tissue or vessels. Thus, when operating in the mesentery, each vessel must be hand-tied in two places with sutures before a cut is made e.g., with scissors between the sutures, a tedious and time consuming process. One commercial product known as the "harmonic scalpel" marketed by Ethicon includes a blade and a coagulator arranged to simultaneously seal and cut sections of tissue and small vessels, thus providing an alternative to the suturing approach. However that device, configured for endoscopic use, is most suitable for procedures such as splenectomy, adrenalectomy, and breast biopsy. It operates rather slowly and its body gets quite warm during operation, raising a risk of damaging nearby tissue. Thus caution must be taken during use to avoid unintentional contact, and the practical length of the operating area is limited, making it unsuitable for many surgeries.

It would therefore be desirable to provide an electrosurgical scalpel and coagulator which operates in other tissue areas and which for example may be used to simultaneously cut and seal multiple vessels of the mesentery. It would further be desirable to provide such an instrument which coagulates quickly while producing little heat in the body of the instrument so that it may be used for prolonged periods in operation on major tissue structures such as the colon, small bowel, lungs, stomach or uterus, as well as smaller structures.

SUMMARY OF THE INVENTION

One or more of the foregoing problems are addressed and advantageous results achieved in an electrosurgical instrument having a handle and a body which position and close a jaw about a tissue site. The jaw includes an electrosurgical cutting member which is biased against a cut line, and an electrode-bearing clamping assembly that clamps a region adjacent the cut line so that the tissue next to the cut is immobilized and dependably sealed in coordination with the cutting procedure.

Preferably, the instrument has the shape of a hemostat with a pair of scissor-like arms defining upper and lower gripping jaws. The upper jaw has a longitudinally extending split or channel in which the electrosurgical cutter such as a blade or wire is positioned and the cutter is biased against an intended cut line extending in the plane gripped by the jaws. The lower jaw has two parallel RF common electrode surfaces, one positioned on each side of the cut line. The two arms of the instrument pivot on an insulating sleeve or bushing to maintain electrical separation therebetween, and the RF power for the cutting blade and the coagulation electrodes is provided through one arm so that all active power is exposed only at small regions at the jaw of that arm. The sealing electrodes are formed of an electrically conductive material, preferably of high thermal conductivity, which may be covered by a thinner coating or thermally non-impeding heat transfer cover, so that tissue in contact therewith is heated to sealing temperature without charring or sticking the tissue at an electrode interface. The coating or cover may include or further carry additional material to assure biocompatibility and to prevent charring and sticking. Preferably the cutting blade or wire is fabricated or coated with an electrically insulating dielectric away from its tissue contacting face, so that fluids which wick into the jaw gap or onto the blade do not introduce new current paths between electrodes, and thus cannot alter or reduce the blade's ability to apply a high energy density at a narrow line for cutting tissue.

The jaws of the device may be extended substantially forward of the blade, which is preferably biased in the direction of jaw closing so that it rides on the tissue. The blade may mount, for example at a slight angle, and can move slightly with respect to the jaw under the bias force, for example, of a leaf spring or a flexure at an anchored end thereof. Preferably, the blade and the sealing electrodes each receive a separate supply of RF energy, which is impedance matched to their particular size and energy transfer requirements. This may be provided by a pair of impedance-matching transformers configured for connection to a common RF source. Alternatively, a transformer having a secondary winding with multiple taps, or a transformer having multiple windings for current and voltage outputs may suitably apportion the total energy applied at the primary between the cutting and sealing electrodes so that each operates with a coordinated time interval to perform its intended task. The transformer or transformers may also have a plurality of taps on the primary side to adapt it for use with different electrosurgical console power supplies. Other power sources may include synthesized and switched circuits to provide RF waveforms of suitable characteristics, rather than such matching or apportioning transformers.

BRIEF DESCRIPTION OF THE DRAWINGS

These and other features of the invention will be understood from the description below taken together with figures illustrative of a preferred embodiment, wherein:

FIGS. 4, 4A–G show another embodiment;

DETAILED DESCRIPTION OF THE INVENTION

Figure 1:
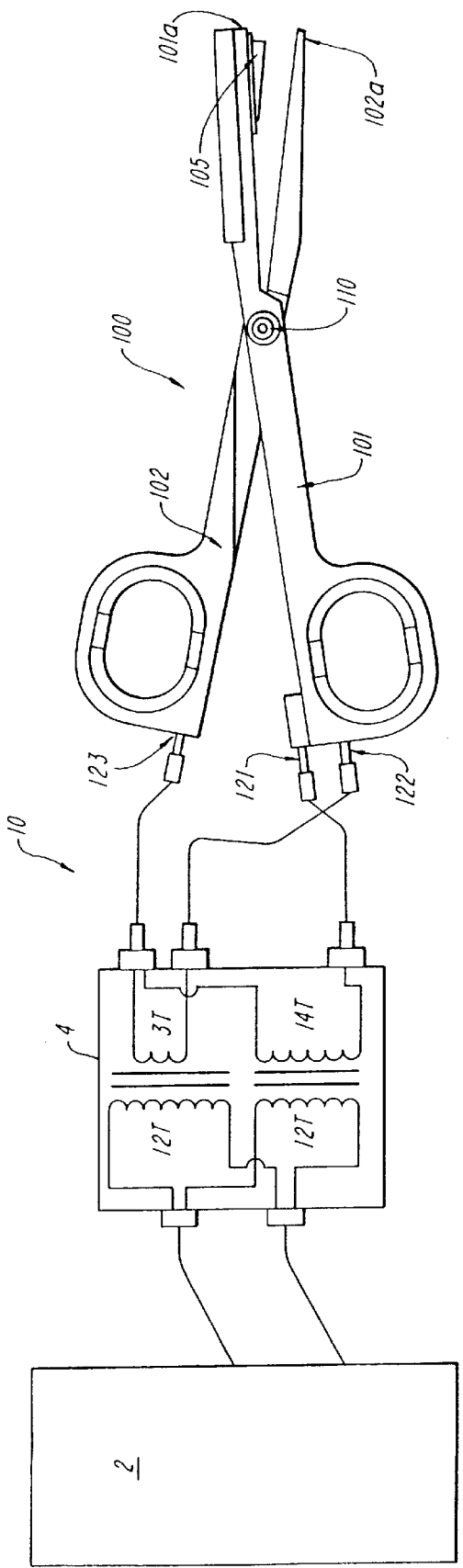
FIG. 1 illustrates an electrosurgical cut and seal instrument and system of the present invention.

FIG. 1 shows a cut and seal surgical tool 100 in a prototype system 10 of the present invention. The system as a whole includes an electrosurgical generator 2, an adaptor 4, and the cut and seal tool 100 which, as illustrated is a hand-held scalpel/sealing assembly. The scalpel/sealer 100 is configured as a forceps or hemostat, with a pair of scissor-like arms 101, 102 that pivot at a pin 110 to bring their jaw ends 101a, 102a together about tissue which is to be cut and sealed.

In the illustrated embodiment, the electrosurgical generator 2 may be a conventional drive unit for a scalpel or sealer which provides a power output which may for example be programmed into or selected by the user for the particular characteristics of the instrument being used. While not specifically illustrated, the generator may include additional input ports for sensors or control devices of various types known in the art. For example, the device may receive a temperature-indicating signal from a thermocouple, or an impedance indicating signal from which the tissue temperature is derived. The drive unit may also determine tissue impedance internally, by measuring the energy flowing in the electrodes of the instrument 100 itself.

Figure 1A:
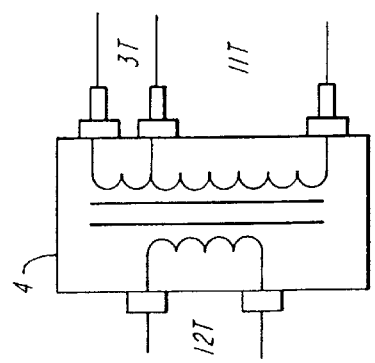
FIG. 1A shows a power adaptor for the instrument of FIG. 1.

The adaptor unit 4 is illustrated as a pair of transformers with parallel primary and respective secondary windings which convert the output of the electrosurgical generator 2 into two drive signals having distinct impedance and signal energy characteristics. While the invention contemplates that the tool 100 may be used with a variety different electrosurgical generators 2 which may themselves each have been designed for a different coagulator or scalpel tool or for a variety of coagulation or cutting tools, the invention also contemplates complete systems wherein a generator 2 is specifically designed for the cutter/sealer 100. In that case the system may include no adapter 4, or such a unit may be incorporated within the generator 2. In addition, the adaptor 4 may take other forms such as solid-state circuits for chopping, dividing or otherwise partitioning electrical energy to apply different signals in appropriate time intervals to the two different sets of electrodes in the tool 100, discussed further below. In a basic embodiment, a single transformer with a tapped secondary as shown in FIG. 1A may also be used to apportion the input energy between the electrodes.

As further shown in FIG. 1, the jaw end of the tool 100 includes a sealing or welding electrode portion (not numbered) extending from the very tip to several centimeters inboard toward the proximal end, and an electrosurgical cutting blade 105 positioned in a central plane through the clamping jaw of the device so that it is urged against tissue in the clamped plane. The jaw 102a forms a common electrode surface for the RF coagulating and cutting electrodes of the jaw 101a.

Figure 2:
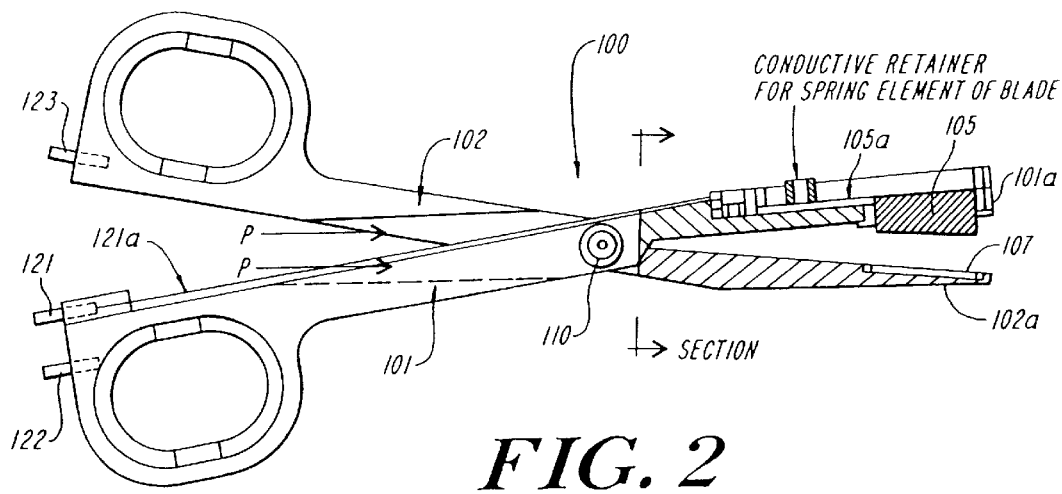
FIG. 2 illustrates a side view of the instrument of FIG. 1.

FIG. 2 illustrates the tool 100 of FIG. 1 in greater detail, with the jaw region shown partially cut away in a vertical central plane passing therethrough. As shown, the arm 102 extends from a proximal end having a scissor-like thumb opening and an RF common electrode connector or plug 123, along a length of its intermediate body to the distal jaw portion 102a. At the very front of the jaw, an insert 107 is positioned in a channel along the length of the jaw below the blade 105 which is mounted on the other arm 101. The insert 107 may, for example, be a polymer which is electrically non-conductive, and provides an anvil, back-stop or tissue support for urging tissue against the blade 105. Blade 105 is aligned to move vertically in a channel extending through the split upper jaw 101a. In this embodiment, the blade is supported by a flex spring shank 105a which is anchored to a conductive retainer close to the pivot 110. As illustrated, the blade 105 is urged downwardly so that it contacts the pad 107 and cuts a straight incision. During operation the tissue remains continuously clamped or held between the opposing jaws 101a, 102a, which thus immobilizes both free ends of the tissue as tension is released by cutting during the procedure.

As further shown in FIG. 2, in the handle of the arm 101, an RF plug or connector 121 connects to a wire 121a which connects to the conductive retainer and spring arm of the cutting blade 105. As illustrated, blade 105 has a relatively long and narrow active electrode or cutting area positioned between the electrode surfaces of the upper clamp jaw.

Figure 3:
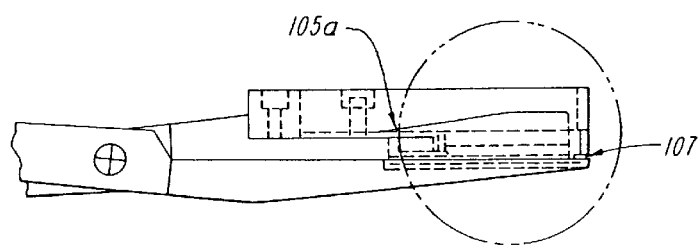
FIG. 3 is a side elevation detail of the tip.
Figure 3A:
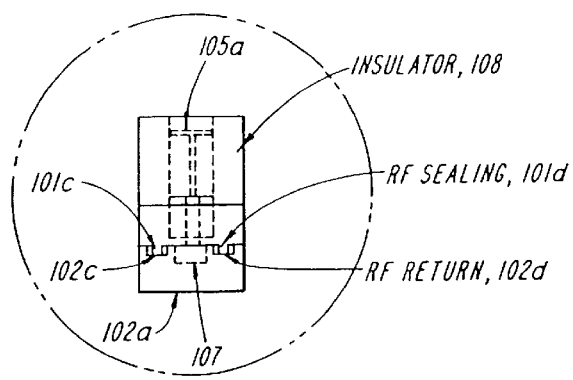
FIG. 3A is an end view thereof from the jaw end.

FIG. 3 illustrates an enlarged view of the jaw end of the tool 100 in a fully closed position. In this position the blade has been urged flat against the insulator pad 107 and tissue is fully severed. As shown in greater detail in the cross-sectional view of FIG. 3A, the insulator pad 107 sits within a U-shaped channel formed in the jaw end 102a so that on each side of the pad a long rectangular strip surface portion of the conductive jaw electrode 102c, 102d presses against the gripped tissue. This exposed region adjacent to the pad 107 constitutes the RF common electrode, which in this embodiment is an integral part of the arm 102. Similarly, the upper jaw, as best seen in FIG. 3A, is vertically divided along its center so that the blade 105 rides freely up and down under influence of its spring arm 105a while the side portions 101c, 110d serve as RF sealing electrodes which are directly opposed to the RF common electrode surfaces of the opposing jaw 102a. A slotted T-shaped insulator block 108 (FIG. 3A) may fit in the split jaw 101a to prevent shorting between the cutting and sealing active electrodes.

As shown in FIG. 2, the RF common connector or plug 123 simply attaches to the conductive arm 102 so that the return path is a large metal structure which generates little localized heating. Similarly, the RF sealing electrodes 101c, 101d (FIG. 3A) are supplied by an RF sealing signal plug or connector 122 which energizes the body of the arm 101 in its entirety. Short circuit between two arms 101, 102 is prevented by their mounting at pivot bushing 110 which as illustrated in greater detail in FIG. 4G, is effected with a spindle-shaped insulating bushing 211a and insulating washers 211b, 211c, or with an insulating grommet through which a metal rivet or bolt 212 passes to secure the arms together. Further insulation may be provided in the facing regions P (FIG. 2) of the respective arms by a polymer insert or a passivation coating fastened or applied to one or both of the respective arms 101, 102.

By way of exemplary materials, the handle and clamping elements may be constructed of copper, aluminum, silver, gold or other suitable heat- and electrically-conductive strong material. The cutting element may be a blade constructed of stainless steel or suitable flex spring material, or may be a wire of suitable shape and electrical/mechanical characteristics such as tungsten wire. Insulating elements may be machined from Teflon, or formed or hardened in situ of suitable polymers or non-conductive ceramics or insulating metallic compounds to provide good wear, frictional and electrical insulation properties.

The coagulation or sealing electrodes 101c, 101d may be separate elements attached to the arm 101 and made of material preferably with good thermal conductivity such as silver, copper, gold or aluminum. These have a somewhat wider surface than the blade, e.g., 1–2 millimeters, and thus provide a thermally conductive reservoir which resists localized heating during extended operation and reduces the occurrence of tissue sticking. This construction results in a low operating temperature which eliminates the risk of damaging nearby tissue structures. For endoscopic use the electrodes are configured so that their maximum temperature does not rise above 50° C. The electrodes may be covered by other materials such as gold, platinum, or even a thin layer or cover of stainless steel, or other material suitable for tissue contact and corrosion resistance. Such outer materials can be plated, welded, swaged, pressed or assembled to the underlying electrode structure. If a tissue contacting material with poor thermal conductivity is used, then preferably it is made as thin as practical to minimize increases in electrode temperature. Any such outer coating or covering is selected to have good electrical conductivity, preferably with a resistivity lower than that of tissue, e.g., less than about 105 ohm-centimeters, and anti-stick coatings such as ME92, or the dense high-chromium alloy coating Al-coat may also be applied.

While the device can be implemented simply using stainless steel as the construction material, stainless steel has relatively poor thermal conductivity, so proper warnings about heating during extended use and the risks involved in contacting surrounding tissue may be usefully included with directions for use.

Preferably the cutting blade region is surrounded by electrically insulating material. This may be effected by applying a plastic insert similar to liner P (FIG. 2) to the inner surfaces of the upper split jaw against which the blade, wire or other cutting element 105 rides. Preferably, however insulation is achieved or improved by coating the blade or cutting element with a continuous layer of insulating material to limit its conductive area to a narrow, tissue-contacting strip. Such coating assures that any fluid wicked into the narrow upper jaw gap will not contact a conductive region of the cutting member or introduce further current paths that would reduce the current density applied at the desired cut line. By spring loading the blade, the blade better adapts to tissue of varying thickness or contour. The cutting element can also be mounted with multiple spring elements or compression areas, or with a pivot mounting to allow it to float and self-align during cutting.

The adaptor unit 4 of FIG. 1 is illustrated as having a first transformer with a large number of turns and high potential applied to the connector 121 for the RF cutting element, and a second transformer with a lower potential winding of fewer turns connected to the arms 101, 102 for powering the sealing electrodes 101c, 101d. In other or further embodiments, the drive circuitry can include control and switching circuitry, which may for example first apply energy to the sealing portion of the device while monitoring the progress of tissue sealing, for example by monitoring tissue impedance, current draw, or actual temperature and relating these in an empirical fashion to the degree of coagulation or sealing achieved. Once sealing is complete, the circuitry then reduces or terminates energy to the sealing portion and applies energy to the cutting element, and may terminate all current once the cutting process is complete. It may further include suitable indicator lights, tone beepers or the like, to indicate procedure status and alarm or reset conditions. As for the sealing process, the cutting process may be controlled by monitoring the impedance or by processing the current passing through the cutting electrode. The controller may further incorporate a programmed cooling dwell time before indicating completion of the procedure. With such feedback control of the ON time of various portions of the tool, the transformer ratio circuit 4 is not necessary, although separate impedance-matching transformer or other elements may be connected to each drive line.

As best seen in the various details of FIGS. 2–3A, the preferred tool 100 has a relatively elongated jaw region, with jaws that are tapered slightly at their tip, and with sealing electrode surfaces extending from the tip back past the blade. This configuration also closes the jaws substantially parallel to grip thick tissue of the mesentery and to apply sealing energy for an extended time over effective strip-like regions bordering the cut line. The construction is comparable to a hemostat, permitting the operator to maintain an effective level of tissue compression which is applied relatively uniformly over an elongated strip like region and may continue even after termination of RF energy or severing of the distal cut line, allowing tissue to cool and the strength of the protein bond in the treated region to increase before complete release of the clamped tissue. In further embodiments, the jaw tips and sealing electrodes may extend more forwardly of the cutter member, allowing a sealing element to operate in front of the cut section and seal ahead of the end of the cut line. The jaw assembly may also be configured as a blunt dissector, for example, tapered in both horizontal and vertical planes to its tip.

FIGS. 4, 4A–4G illustrate views of another embodiment 200 of the seal and cut instrument of the present invention, including a side view 4, a top view 4A and vertical sectional view 4B as well as end views 4C, 4D, perspective views 4E, 4F, and an exploded assembly view 46. For convenience of illustration, the tool 200 is shown in an inverted top/bottom orientation from that of tool 100 (FIG. 2) but is otherwise substantially similar. As shown in the exploded view, FIG. 4G, the cutting electrode assembly is advantageously implemented with a disposable and replaceable set of elements including a flex blade 205 and insulation guide or liner 207 which advantageously snap into or fasten onto the nose of one of the opposing clamp jaw pieces. The elements 205, 207 may also be replaced by a preassembled cartridge assembly, wherein the blade is embedded, for example, in a slide-on insulating block carrier assembly, or a bolt-on cartridge as shown in FIG. 5H. The two arms of the instrument are electrically isolated from each other. This may be effected by a construction wherein metal-to-metal contact is prevented.

Figure 5A:
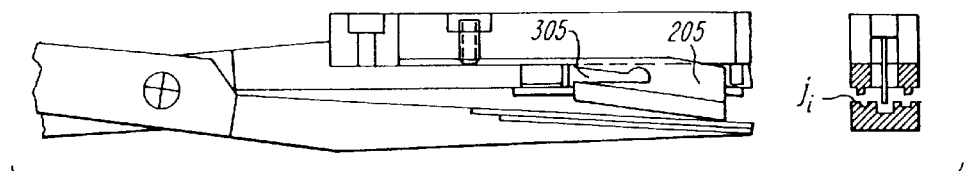
FIGS. 5A–5I illustrate alternative electrode and jaw constructions.
Figure 5B:
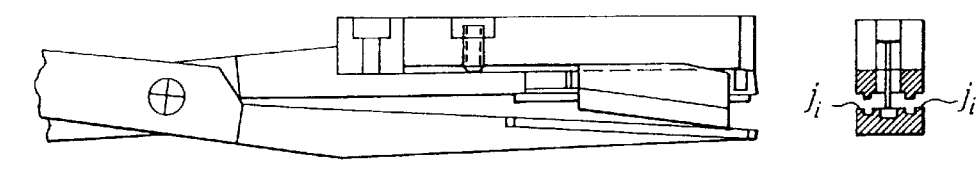
Figure 5C:
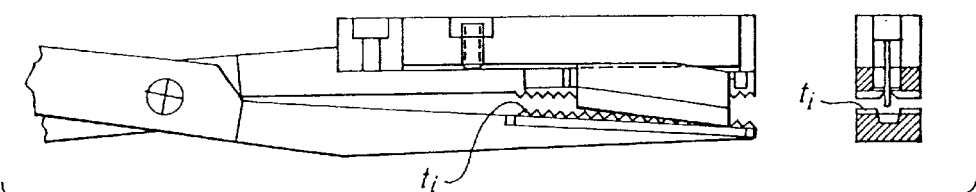
Figure 5D:
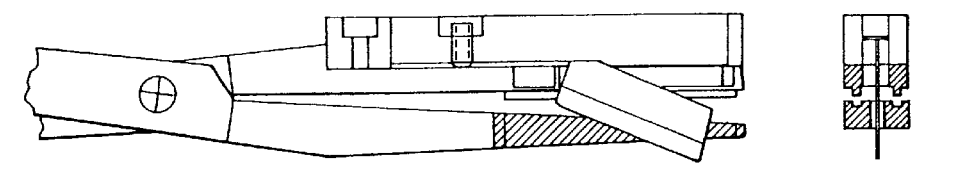
Figure 5E:
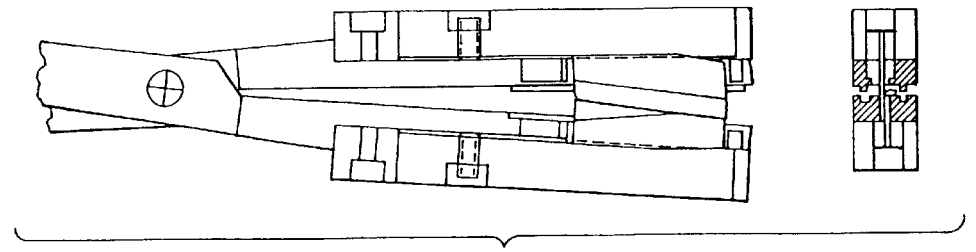
Figure 5F:
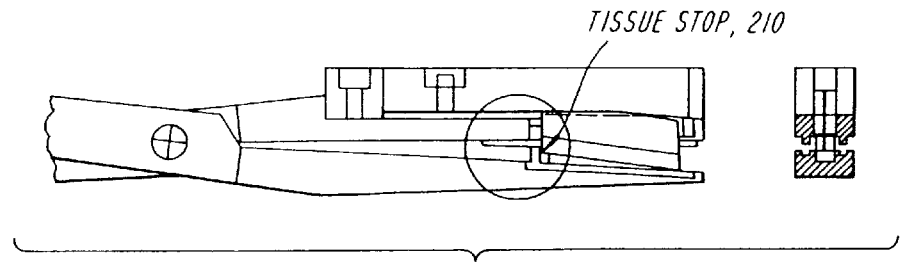
Figure 5G:
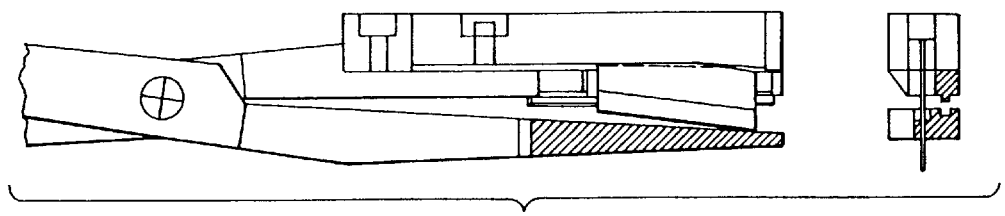
Figure 5H:
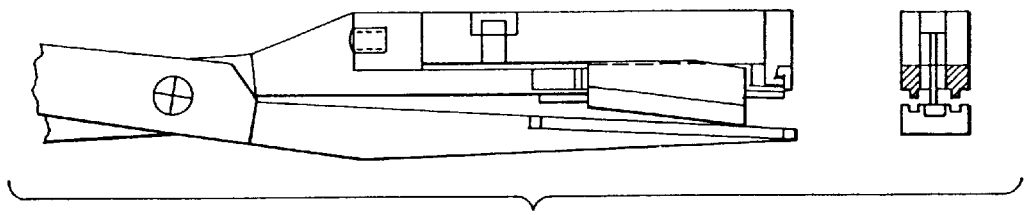
Figure 5I:
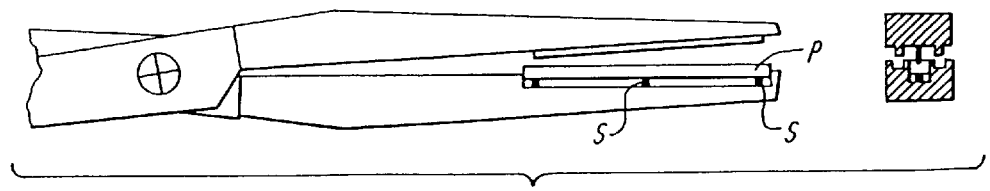

FIGS. 5A–5I each show a further embodiment of the seal and cut tool of the present invention. Each of these figures illustrates an enlarged side view of the jaw portion in a partially open state, together with an end view, as seen from the nose end, to display the fitting of opposed pieces and the use of insulating material in the blade mounting. As shown in FIG. 5A, the electrode surfaces of the jaws may have longitudinal serrations $j_i$ to grip tissue and better urge the electrode surfaces into conductive contact. The blade 205 may have a relief cut 305 so that it is suspended by a relatively narrow body portion and flexes to self-align when it is urged against tissue. Self-alignment may also be provided by a multiple-spring suspension. FIG. 5B illustrates a substantially similar construction with a standard blade of solid sheet construction, again having longitudinally serrated jaws. As shown in FIG. 5C, the jaws may alternatively be provided with transverse serrations $t_i$. The tool may also be configured so that the blade suspended from one jaw passes through a slot in the opposed jaw, in the manner of a guillotine, as shown in FIG. 5D, or so that a blade electrode is positioned in each jaw to effect cutting from opposed sides (FIG. 5E). In other embodiments, the tip is configured to define specialized cuts, for example, by providing a tissue stop 210 (FIG. 5F) to limit the reach of the blade from a tissue edge, thus assuring that the blade does not cut an isolated "buttonhole", or by providing a sealing electrode on a single side of the blade 205, as shown in FIG. 5G. In this case, the clamping preferably also occurs only on that side. The latter construction is especially useful, for example, for surgery to resect lung or other tissue wherein some tissue is excised by the cut for pathology examination, while the remainder of tissue on the other side of the cut remains in the body to heal or be resorbed. In this case, the single-side sealing electrode seals the cut to prevent bleeding, without denaturing or mechanically bruising the tissue specimen removed for pathology examination. Furthermore, in any of the foregoing embodiments, the blade need not be spring-loaded. It may be rigidly affixed to the jaw as shown in FIG. 5I, with a counter-anvil, such as a polymer strip "P", nominally positioned on the opposed jaw, to urge tissue against the blade. In that case, the strip may be suspended on expansion or leaf springs "S" to force the tissue against the cutting electrode.

Figure 6A:
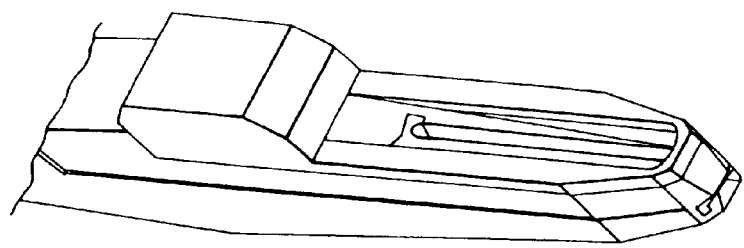
FIGS. 6A–6C illustrate jaw shapes of further embodiments.
Figure 6C:
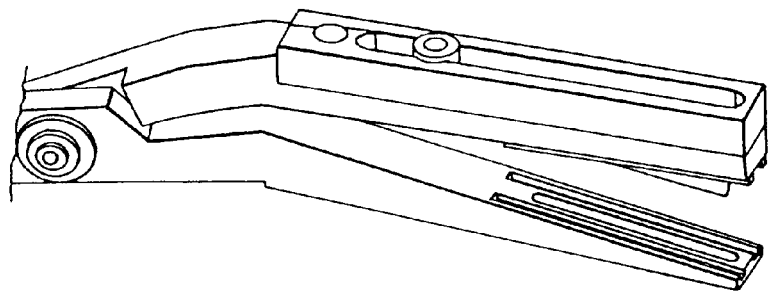
Figure 6B:
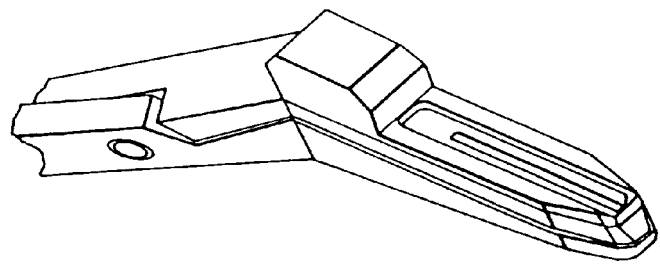

In addition to these variations of blade and electrode configurations, it will be understood that the jaws of the tool may be formed in diverse shapes, such as the blunt nose of FIG. 6A, or the angled tip of FIG. 6B. The latter configuration with the tip angled out of the nominal plane of the tool assures visibility of the working region of the clamp. Similarly, as shown in FIG. 6C, the tip may be angled in the plane of the tool to allow the central axis of the handle to be held at an angle or offset with respect to the cut plane, facilitating manipulation in the surgical arena.

Advantageously, in any of the foregoing embodiments, the handles or arms of the tool may include a ratchet arm which locks the jaws in their clamped position, in the manner of a hemostat. Furthermore, the structural body, e.g., the handle, jaw and intermediate portions, may carry an electrically insulating coating on all but the electrode surfaces in order to avoid the occurrence of irregular shunt paths when wetted by blood or saline in the operating arena.

Figure 7:
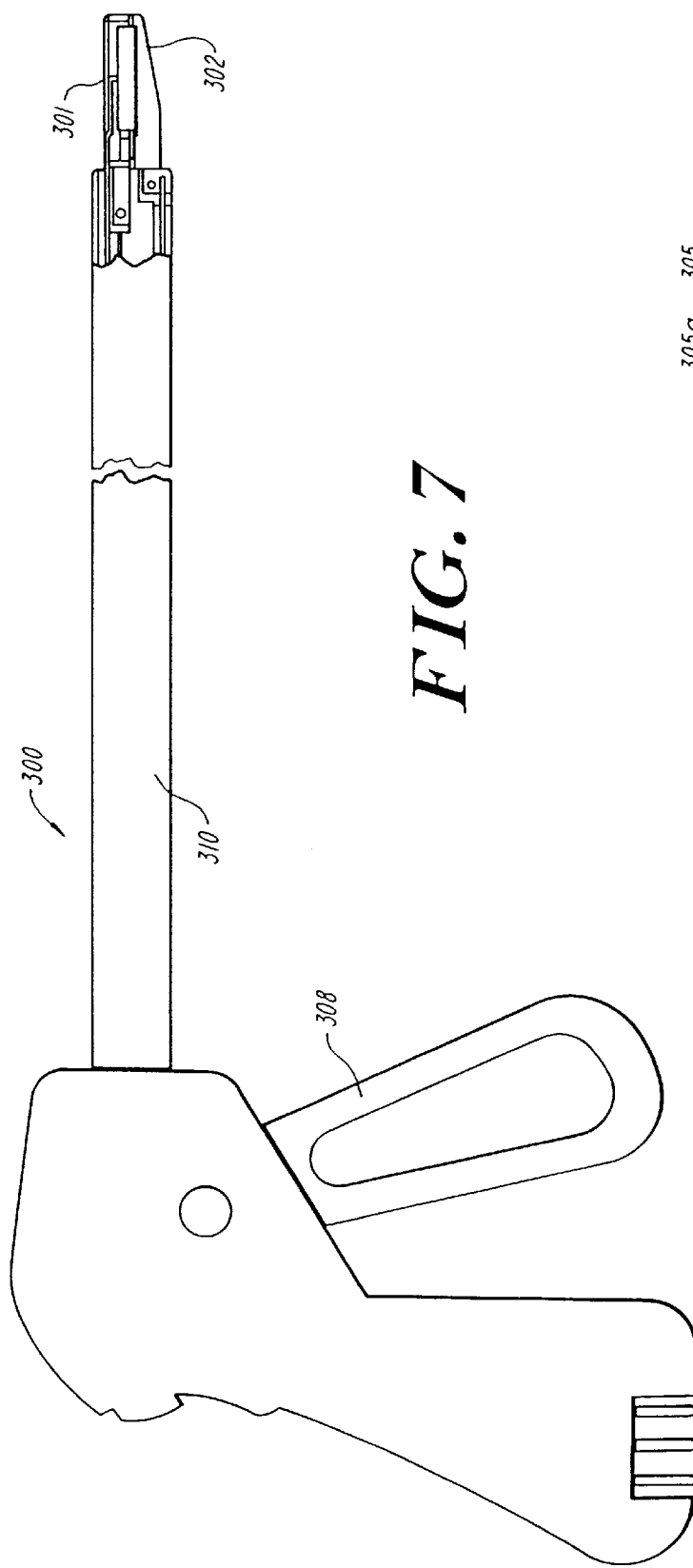
FIGS. 7 and 7A illustrate an endoscopic embodiment of the invention.
Figure 7A:
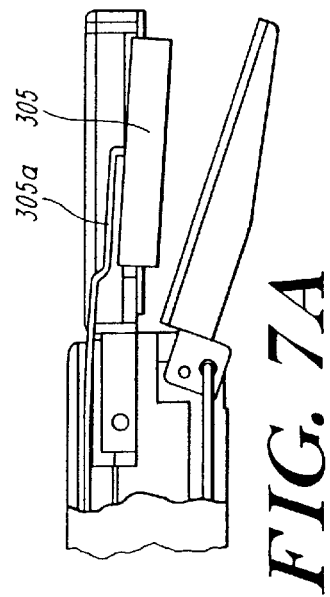

The invention also contemplates embodiments adapted for endoscopic use, such as the embodiment 300 of FIG. 7. As shown in that figure, upper and lower jaws 301, 302 are configured to clamp together via a handle actuation mechanism 308 which is mechanically coupled through an elongated body 310. In the multi-part mechanical construction of this device, an electrode lead 305a may travel through the body 310 to the blade 305, and one or more of the jaws may be carried by an electrically insulated mounting to isolate it from the other. FIG. 7A shows an enlarged view of the clamp assembly with the jaws open.

For either the endoscopic or the first-described embodiments above, the electrical components of the device, beyond a single wire or conductor for energizing the blade, may advantageously take several forms. In one embodiment, an interlock may be provided to prevent one or more of the electrodes from being energized before the jaws are closed. This may be implemented by a switch mounted in the tool itself, or by a sensor on the tool coupled to a switching and detection circuit in the RF console or driver. Push button switches on the handle may be connected to control the RF power and allow the user to select a sealing, a cutting or a seal and cut operating cycle.

Furthermore, the blade itself need not be a conductor. It may be implemented as a non-conductive member, with a conductive wire or strip mounted or coated along a desired cutting edge. Alternatively, it may be configured as an entirely sealed or insulated capacitive element which couples capacitively to tissue to effect the RF current flow for performing its cutting action.

Furthermore, the instrument may be provided with a temperature indicating device, or a thermally-responsive safety or actuation device. For example, the tool may have a thermochromic coating which changes color to indicate when the body of the device is approaching a dangerously hot temperature (e.g. 45–50° C.). Alternatively, a thermosensor or a bimetallic switch may be configured to display temperature, or temperature threshold, to sound a warning, or to selectively activate the cutting electrode when an adequate sealing temperature has been attained. The latter construction is especially advantageous in a laparoscopic instrument.

Systems of the present invention may include various forms of programmed or feedback-controlled RF driver circuitry, that may operate, for example to first seal, then cut, the clamped tissue. Such control systems may also adjust the level of applied power to correspond to the tissue impedance or other relevant parameter of the clamped tissue.

The adaptor 4 (FIG. 1) may be configured to match the electrodes of the tool to either a monopolar or bipolar RF source, adapting the lower or higher impedance source, respectively, to each of the electrodes.

The invention being thus disclosed and described, further variations and modifications will occur to those skilled in the art, and all such variations and modifications are considered to be within the spirit and scope of the invention, as defined by the claims appended hereto and equivalents thereof.

What is claimed is:

1. An electrosurgical instrument for tissue surgery, such instrument comprising an elongated surgical tool having a handle, a body and a jaw assembly, the handle and body being operable to position the jaw assembly about an intended site for cutting through tissue at the site, and wherein the jaw assembly includes an electrosurgical cutting member, and a clamping assembly formed of opposed jaw members and effective for clamping a plane region of tissue adjacent to a cut line, positioning the tissue against the cutting member along said cut line, said clamping assembly further including electrosurgical sealing electrodes for heating said plane region to seal along the length of a cut and said electrosurgical cutting member being movably biased against the cut line so that the cutting member automatically severs the tissue clamped in said plane region.

2. An electrosurgical instrument according to claim 1, wherein the clamping assembly includes a first set of clamping jaw surfaces, and a second set of clamping jaw surfaces extending parallel to said first set of clamping jaw surfaces wherein said handle is operative to clamp said first and second set of clamping jaw surfaces so as to effectively prevent tissue movement as tension is released during cutting so that said tissue remains immobilized for effective sealing.

3. An electrosurgical instrument according to claim 2, wherein said movable cutting member is a spring biased blade or wire.

4. An electrosurgical instrument according to claim 3, wherein the first and second set of clamping jaw surfaces form a split jaw of a hemostat, and said spring biased blade or wire is mounted in a split between the surfaces of the jaw.

5. An electrosurgical instrument according to claim 2, wherein said cutting member and clamping assembly are dimensioned for coagulating and cutting mesentery tissue.

6. An electrosurgical instrument according to claim 2 configured as a hemostat with a pair of pivotally joined arms, and wherein one arm is a conductive arm forming a common RF electrode for said cutting member and said sealing electrodes, and the other arm carries said cutting member and said sealing electrodes.

7. An electrosurgical instrument according to claim 6, wherein said arms are joined by an electrically insulating pivot assembly.

8. An electrosurgical instrument according to claim 6, wherein said cutting member has a tissue cutting edge, and is insulated by an electrically insulating coating away from the edge thereby localizing current at said edge.

9. An electrosurgical instrument according to claim 6, wherein said first and second sets of clamping jaw surfaces are defined by first and second sides of a pair of split jaw members, a first split jaw member carrying the cutting member in an elongated medial slot thereof, and the second split jaw member carrying a counter-block formed of insulating material in an elongated central slot.

10. An electrosurgical instrument according to claim 9, wherein said second split jaw member is a conductive member connected as a RF common for electrosurgical energy applied to said cutting member and to the clamping jaw surfaces of said first split jaw member.

11. An electrosurgical instrument according to claim 1, wherein the clamping assembly includes sealing electrodes formed of thermally conductive material.

12. An electrosurgical instrument according to claim 11, wherein said thermally conductive material is covered by one or more of a) a thermally non-impeding cover and b) a non-stick cover.

13. An electrosurgical instrument according to claim 1, wherein said handle, body and jaw are configured as a hemostat.

14. An electrosurgical instrument according to claim 1, further comprising an energy ratio input element for proportioning electrosurgical energy to said cutting member and said coagulation electrodes.

15. An electrosurgical instrument according to claim 14, wherein the energy ratio input element i) matches output characteristics of an RF source to input impedances of said cutting member and of said sealing electrodes of the clamping assembly, and ii) provides an RF signal of higher voltage to said cutting member than to said sealing electrodes.

16. An electrosurgical instrument according to claim 1, wherein the body is an elongated body which configures the instrument for minimally invasive surgery such that the handle operates said clamping assembly through the body without spreading the body.

17. An electrosurgical instrument according to claim 1, further comprising a thermochromic coating for visibly indicating temperature of said instrument.

18. An electrosurgical instrument according to claim 1, wherein said sealing electrodes seal along a single side of the cut to excise a tissue sample without denaturing the sample.

* * * * *

UNITED STATES PATENT AND TRADEMARK OFFICE
CERTIFICATE OF CORRECTION

PATENT NO. : 6,174,309 B1  
DATED : January 16, 2001  
INVENTOR(S) : Thomas A. Wrublewski, Kevin M. Allaire, William Frey, and Kevin Lemire Page 1 of 1

It is certified that error appears in the above-identified patent and that said Letters Patent is hereby corrected as shown below:

<u>Column 6,</u>  
Line 42, reads "an exploded assembly view 46", should read -- an exploded assembly view 4G --

Signed and Sealed this

Nineteenth Day of March, 2002

Attest:

JAMES E. ROGAN  
*Attesting Officer*  *Director of the United States Patent and Trademark Office*